(12) United States Patent
O'Lenick

(10) Patent No.: US 8,580,999 B1
(45) Date of Patent: Nov. 12, 2013

(54) CITRATE ESTER EMULSIFIERS

(75) Inventor: Thomas G. O'Lenick, Dacula, GA (US)

(73) Assignee: SurfaTech Corporation, Lawrenceville, GA (US)

( * ) Notice: Subject to any disclaimer, the term of this patent is extended or adjusted under 35 U.S.C. 154(b) by 96 days.

(21) Appl. No.: 13/374,715

(22) Filed: Jan. 10, 2012

(51) Int. Cl.
*C07C 69/66* (2006.01)

(52) U.S. Cl.
USPC .......................................................... 560/182

(58) Field of Classification Search
USPC .............................................................. 560/1
See application file for complete search history.

(56) References Cited

U.S. PATENT DOCUMENTS

| | | |
|---|---|---|
| 4,868,236 A | 9/1989 | O'Lenick |
| 6,403,825 B1 * | 6/2002 | Frappier et al. ............... 560/180 |
| 2006/0188802 A1 * | 8/2006 | Koyama et al. ............ 430/108.4 |

OTHER PUBLICATIONS

O'Lenick, Parkinson, Butta vol. 110 Aug. 1995 Guerbit Citrate Esters Allhred IL.

* cited by examiner

*Primary Examiner* — Wu-Cheng Winston Shen
*Assistant Examiner* — Blaine G Doletski

(57) ABSTRACT

The present invention is directed to a series of citrate ester emulsifiers that are effective in making water in oil (regular emulsions) and oil in water (invert emulsions). In addition to being outstanding emulsifiers, these emulsifiers provide unique solubility, liquidity and outstanding feel when applied to the skin, making them highly desirable in cosmetic emulsions.

2 Claims, No Drawings

CITRATE ESTER EMULSIFIERS

GOVERNMENT SPONSORSHIP

None

FIELD OF THE INVENTION

The present invention is directed to a series of citrate ester emulsifiers that are effective in making water in oil (regular emulsions) and oil in water (invert emulsions). In addition to being outstanding emulsifiers, these emulsifiers provide unique solubility, liquidity and outstanding feel when applied to the skin, making them highly desirable in cosmetic emulsions.

BACKGROUND OF THE INVENTION

Citric acid is a common material of natural origin. The structure is:

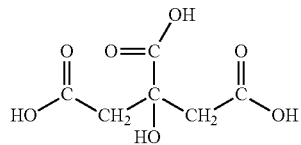

CAS Registry number: 77-92-9
CAS Index name: 1,2,3-Propanetricarboxylic acid

Citric acid is made during the fermentation process; using cultures of *Aspergillus niger* are fed on a sucrose or glucose-containing medium.

Citric acid is one of a series of compounds involved in the physiological oxidation of fats, proteins, and carbohydrates to carbon dioxide and water. This series of chemical reactions is central to nearly all metabolic reactions, and is the source of two-thirds of the food-derived energy in higher organisms. Krebs received the 1953 Nobel Prize in physiology or Medicine for the discovery. The series of reactions is known by various names including, citric acid cycle, the Krebs cycle, and the tricarboxylic acid cycle.

Citrate esters are also well known. They conform to the following structure:

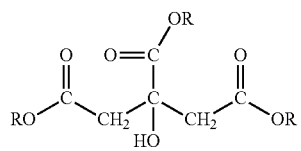

These esters are made by the reaction of citric acid with alcohols.

U.S. Pat. No. 4,292,192 issued to Hooper et al. teaches that detergent bars for personal washing are given a deodorant property by including an ester of citric acid. The ester maybe an acetyl derivative. The amount of ester used will be in the range of 0.3% to 3.0%. Examples of the esters are triethyl citrate and acetyl tributyl citrate.

An article published in Cosmetic and Toiletries Magazine (Vol. 110 August 1995) by O'Lenick et al addresses Guerbet Citrate Esters. It specifically deals with oil phase emollient esters and breathable non occlusive esters that have fluoro components contained in the ester. Both type of esters are hydrophobic (i.e. oil loving). This article discloses the state of the art of citrate esters, specifically as oil soluble materials that can be applied to skin. The article is posted on http://www.surfatech.com/pdfs/Guerbet%20Citrate%20Ester%20Article.pdf The ability to make compounds having differing solubility in water allows one to make surface active agents, or surfactants. The proper selection of the ratio of water soluble to oil soluble material in the molecule allows for the manufacture of emulsifiers useful over a wide range of formulations.

HLB is a methodology that explains this phenomenon. The method was developed by Griffin in 1954 and relates an estimation of surfactant properties to the percentage of water soluble group in a molecule. Specifically, the system addresses polyoxyethylene groups in a non-ionic surfactant/

HLB=% PEG in the molecule/5

HLB value of 0 corresponds to a completely hydrophobic molecule, and a value of 20 would correspond to a molecule made up completely of hydrophilic components.

The HLB value can be used to predict the surfactant properties of a molecule:
A value from 4 to 8 indicates an anti-foaming agent
A value from 7 to 11 indicates a W/O (water in oil) emulsifier
A value from 12 to 16 indicates oil in water emulsion
A value from 11 to 14 indicates a wetting agent
A value from 12 to 15 is typical of detergents
A value of 16 to 20 indicates a solubiliser or hydrotrope.

The citrate esters known prior to the compounds of the present invention are oil phases. It was previously unappreciated that by making specific heretofore unknown esters, a series of citrate esters could be developed that are emulsifiers. There has been a long felt need for emulsifiers that provide excellent emulsification and citrate esters have not been available that had any water soluble groups, until this invention.

THE INVENTION

Object of the Invention

The current invention is directed toward a series of citrate esters that contain polymeric alkoxylated groups that allow for the preparation of a series of emulsifiers that range from water soluble (HLB over 10) for making oil in water emulsions, to products that have less water soluble groups that are water dispersible having HLB of around 3 allowing one to make water in oil emulsions.

SUMMARY OF THE INVENTION

The compounds of the present invention are citrate esters that have differing amounts of polyoxypropylene groups and fatty groups present on the citrate molecule.

There are two necessary requirements to make the compounds of the present invention (1) the citrate ester must be made with alkoxylated methyl alcohol (thereby blocking one end of the group and prohibiting cross linking) and (2) the citrate ester must have at least one fatty group to make the molecule surface active.

The reaction of PEG (polyoxyethylene) with citrate results in polymers that are solids and not useful in the present invention. The fact that PEG compounds contain two hydroxyl groups (OH) they will react with the citric acid, which has three reactive carboxyl groups (COOH) to make polyesters.

H—(OCH$_2$CH$_2$)$_9$OH PEG 400 Two reactive OH groups

H—(OCH$_2$CH$_2$)$_9$OCH$_3$ PEG 400 One Reactive OH group

DETAILED DESCRIPTION OF THE INVENTION

The citrate esters of the present invention conform to the following structure:

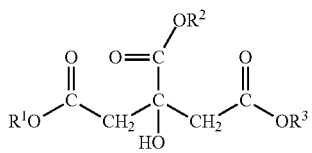

wherein;
$R^1$ $R^2$ and $R^3$ are independently selected from the group consisting of —(CH$_2$CH$_2$O)$_a$CH$_3$ and alkyl having 8 to 26 carbon atoms, with the proviso that $R^1$ $R^2$ and $R^3$ are all —(CH$_2$CH$_2$O)$_a$CH$_3$ or alkyl having 8 to 26;
a is an integer ranging from 5 to 25

Preferred Embodiments

In one preferred embodiment the citrate ester is a mono alkyl citrate ester conforming the following structure:

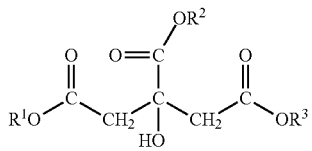

wherein;
$R^1$ and $R^2$ are —(CH$_2$CH$_2$O)$_a$CH$_3$;
$R^3$ is alkyl having 8 to 26 carbon atoms
a is an integer ranging from 5 to 25.

In another preferred embodiment the citrate ester is a di alkyl citrate ester conforming the following structure

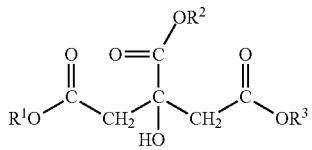

wherein;
$R^1$ is —(CH$_2$CH$_2$O)$_a$CH$_3$;
$R^3$ and $R^2$ are alkyl having 8 to 36 carbon atoms;
a is an integer ranging from 5 to 25.

Examples

Raw Materials
Poly(Ethylene Glycol) Monomethyl Ether
Poly(ethylene glycol) monomethyl ether is commercially available from a variety of sources one of which is FCI Technology of Gastonia, N.C. It conforms to the following structure;

CH$_3$(CH$_2$CH$_2$O)$_a$—H wherein;
a is an integer from 5 to 25;

| Example | a | Molecular Weight (g/mol) |
|---|---|---|
| 1 | 5 | 237 |
| 2 | 8 | 367 |
| 3 | 15 | 676 |
| 4 | 23 | 1027 |
| 5 | 25 | 1116 |

Fatty Alcohols

Fatty alcohols are useful in the practice of the present invention are items of commerce they are available as either single components or mixtures.

Fatty alcohols are useful as raw materials in the preparation of compounds of the present invention are commercially available from a variety of sources including Procter and Gamble of Cincinnati Ohio.

The structures are well known to those skilled in the art.

R—OH

Saturated

| Saturated | | | |
|---|---|---|---|
| Example | R Formula | Common Name | Molecular Weight |
| 6 | C$_8$H$_{18}$ | Capryl | 130 |
| 7 | C$_{10}$H$_{22}$ | Capric | 158 |
| 8 | C$_{12}$H$_{25}$ | Lauryl | 186 |
| 9 | C$_{14}$H$_{30}$ | Myristyl | 214 |
| 10 | C$_{15}$H$_{32}$ | Pentadecyl | 229 |
| 11 | C$_{16}$H$_{34}$ | Cetyl | 243 |
| 12 | C$_{18}$H$_{36}$ | Stearyl | 269 |
| 13 | C$_{20}$H$_{40}$ | Arachidyl | 297 |
| 14 | C$_{22}$H$_{44}$ | Behenyl | 325 |
| 15 | C$_{26}$H$_{52}$ | Cetryl | 381 |
| 16 | C$_{34}$H$_{68}$ | Geddyl | 493 |
| Unsaturated | | | |
| Example | R Formula | Common Name | Molecular Weight |
| 17 | C$_{18}$H$_{36}$ | Oleyl | 268 |
| 18 | C$_{18}$H$_{34}$ | Linoleyl | 266 |

Guerbet Alcohols

Guerbet alcohols useful as raw materials in the preparation of compounds of the present invention are commercially available from a variety of sources including Sasol North America Incorporated of Houston Tex.

The structures are well known to those skilled in the art.

y is an integer ranging from 3-15 and x is an integer ranging from 5-17.

| Example | y | x |
|---------|----|----|
| 19 | 15 | 17 |
| 20 | 3  | 5  |
| 21 | 9  | 7  |

Citric Acid

Citric acid is an item of commerce available from a variety of sources including Pfizer. It conforms to the following structure:

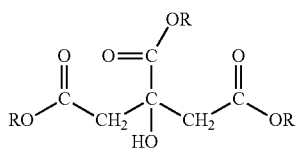

Citric acid is 2-hydroxypropane-1,2,3-tricarboxylic acid and has a CAS number of 77-92-9.

Compounds of the Present Invention

Poly(Ethylene Glycol) Monomethyl Ether Citrate Esters

Citrate esters were prepared by SurfaTech Corporation, of Lawernceville, Ga. They are made by the esterification reaction of citric acid and methoxy-poly (ethylene glycol). Poly (ethylene glycol) monomethyl either is commercially available from FCI Technology of Gastonia, N.C. They conform to the following structure;

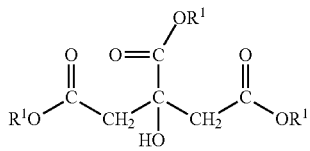

wherein;
$R^1$ is $-O(CH_2CH_2O)_aCH_3$
a is an integer ranging from 5 to 25;

Examples

Esterification Reactions

In addition to the molecular weight of polyethylene glycol) monomethyl ether (MePEG), it is very important for the practice of the current invention resulting in a compound of the present, to have the correct ratio of fatty groups to MePEG groups.

General Procedure

To the specified number of grams of citric acid is added to a specified amount of MePEG (Examples 2-5) and the specified number of grams of alcohol (Examples 6-21). The reaction mixture is heated to 160-180° C. Water is removed by vacuum during the reaction process. The reaction is monitored by determination of acid value. The acid value will diminish as the reaction proceeds. The reaction is cooled once the acid value fails to change over an additional two hours at temperature. The product is used without purification.

Mono Alkyl Citrate Esters

|  | MePEG | | Fatty Alcohol | | Citric Acid |
|---------|---------|-------|---------|-------|-------|
| Example | Example | Grams | Example | Grams | Grams |
| 22 | 2 | 58.7 | 21 | 25.2 | 16.1 |
| 23 | 2 | 64.9 | 20 | 17.3 | 17.8 |
| 24 | 2 | 60.2 | 12 | 23.2 | 16.5 |
| 25 | 2 | 47.2 | 19 | 39.9 | 12.9 |
| 26 | 4 | 80.3 | 21 | 12.0 | 7.7 |
| 27 | 4 | 81.2 | 12 | 11.0 | 7.8 |
| 28 | 4 | 84.1 | 20 | 7.8 | 8.1 |
| 29 | 4 | 71.8 | 19 | 21.3 | 6.9 |

Di Alkyl Citrate Esters

|  | MePEG | | Fatty Alcohol | | Citric Acid |
|---------|---------|-------|---------|-------|-------|
| Example | Example | Grams | Example | Grams | Grams |
| 30 | 2 | 30.6 | 21 | 52.5 | 16.8 |
| 31 | 2 | 38.3 | 20 | 40.7 | 21.0 |
| 32 | 2 | 32.3 | 12 | 49.9 | 17.7 |
| 33 | 2 | 20.3 | 19 | 68.6 | 11.1 |
| 34 | 4 | 55.8 | 21 | 33.5 | 10.7 |
| 35 | 4 | 57.7 | 12 | 31.2 | 11.1 |
| 36 | 4 | 63.9 | 20 | 23.8 | 12.3 |
| 37 | 4 | 42.1 | 19 | 49.8 | 8.1 |

Applications Examples

Emulsification

Emulsifier Test Procedure

| Material | % Wt |
|----------|------|
| Water | 47.0 |
| Soybean Oil | 47.0 |
| Emulsifier | 5.0 |
| Salt | 1.0 |

Procedure:
1. Place emulsifier or emulsifier blend into the oil phase.
2. Mix well, noting clarity.
3. Add salt to water phase.
4. Heat both phases to 50° C.
5. Add water phase to oil phase and using mixer mix for 120 seconds.
6. Note appearance.

Results

Example 22 and example 29 both gave a stable oil in water emulsion

Example 30 and 33 both gave a stable water in oil emulsion.

All emulsions were not sticky on the skin and gave a good dry feel.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A mono alkyl citrate ester having the following structure:

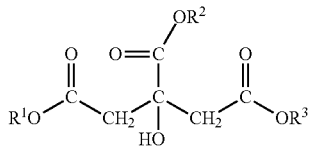

wherein;

R$^1$ and R$^2$ are —(CH$_2$CH$_2$O)$_a$CH$_3$;

R$^3$ is alkyl having 8 to 26 carbon atoms;

a is an integer ranging from 5 to 25.

2. A dialkyl citrate ester having the following structure:

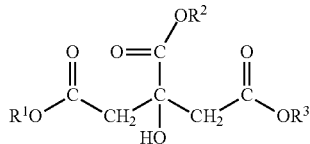

wherein;

R$^1$ is —(CH$_2$CH$_2$O)$_a$CH$_3$;

R$^2$ and R$^3$ are alkyl having 8 to 36 carbon atoms;

a is an integer ranging from 5 to 25.

* * * * *